(12) United States Patent
Leeflang et al.

(10) Patent No.: US 12,357,809 B1
(45) Date of Patent: *Jul. 15, 2025

(54) VALVES AND HUBS FOR TUBULAR DEVICES AND METHODS FOR MAKING AND USING THEM

(71) Applicant: CLPH, LLC, Palo Alto, CA (US)

(72) Inventors: Stephen Arie Leeflang, Sandy, UT (US); Brendan Marshall O'Neill, San Jose, CA (US); Christian Scott Eversull, Palo Alto, CA (US)

(73) Assignee: CLPH, LLC, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/080,650

(22) Filed: Dec. 13, 2022

Related U.S. Application Data

(63) Continuation of application No. 16/436,873, filed on Jun. 10, 2019, now Pat. No. 11,524,152.

(60) Provisional application No. 62/682,534, filed on Jun. 8, 2018.

(51) Int. Cl.
*A61M 39/22* (2006.01)
*A61M 25/00* (2006.01)
*A61M 39/24* (2006.01)

(52) U.S. Cl.
CPC ...... *A61M 39/227* (2013.01); *A61M 25/0009* (2013.01); *A61M 25/0097* (2013.01); *A61M 2039/2426* (2013.01)

(58) Field of Classification Search
CPC ............ A61M 39/227; A61M 25/0009; A61M 25/0097; A61M 2039/2426
See application file for complete search history.

(56) References Cited

U.S. PATENT DOCUMENTS

| | | | | |
|---|---|---|---|---|
| 4,895,346 | A * | 1/1990 | Steigerwald | F16K 7/20 604/167.04 |
| 5,006,113 | A * | 4/1991 | Fischer | A61M 39/0606 604/167.04 |
| 5,549,576 | A * | 8/1996 | Patterson | A61M 25/0662 604/247 |
| 7,081,106 | B1 * | 7/2006 | Guo | A61M 39/06 604/167.04 |
| 8,529,523 | B2 * | 9/2013 | Weaver | F16K 15/147 604/167.03 |
| 11,524,152 | B1 * | 12/2022 | Leeflang | A61M 25/0097 |
| 2001/0049499 | A1 * | 12/2001 | Lui | A61M 39/06 604/167.04 |
| 2004/0210194 | A1 * | 10/2004 | Bonnette | A61B 17/22 604/167.06 |

* cited by examiner

*Primary Examiner* — Theodore J Stigell
(74) *Attorney, Agent, or Firm* — William A. English; Vista IP Law Group LLP

(57) ABSTRACT

A valve is provided for a sheath, catheter, or other tubular device that includes a first face, a second face opposite the first face and an axis extending between the first and second faces. A first slit extends substantially parallel to the axis from the first face towards the second face to a first intermediate location within the valve body, a second slit extends substantially parallel to the axis from the second face towards the first face to a second intermediate location within the valve body, and a bore extends along the axis between the first intermediate location and the second intermediate location.

24 Claims, 9 Drawing Sheets

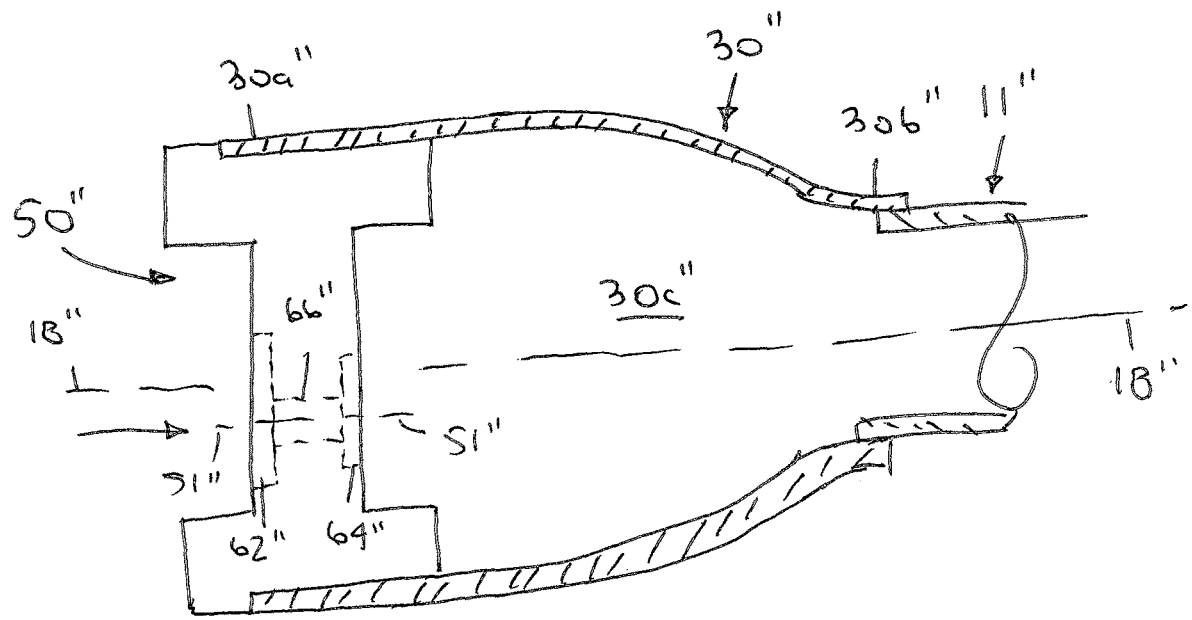
FIG. 1C
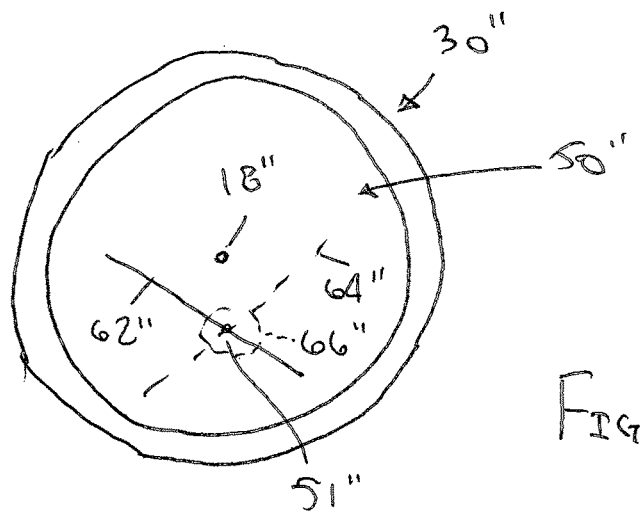
FIG 1C(1)

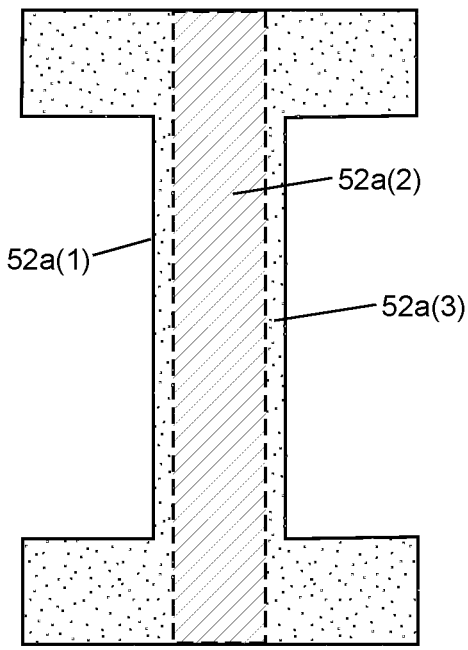
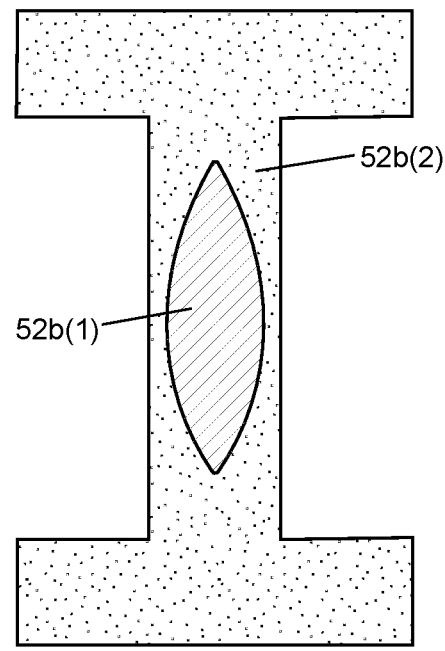
FIG. 5A  FIG. 5B
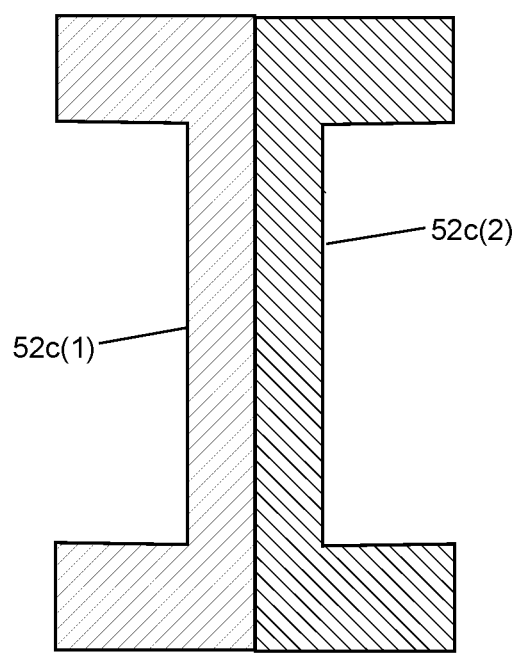
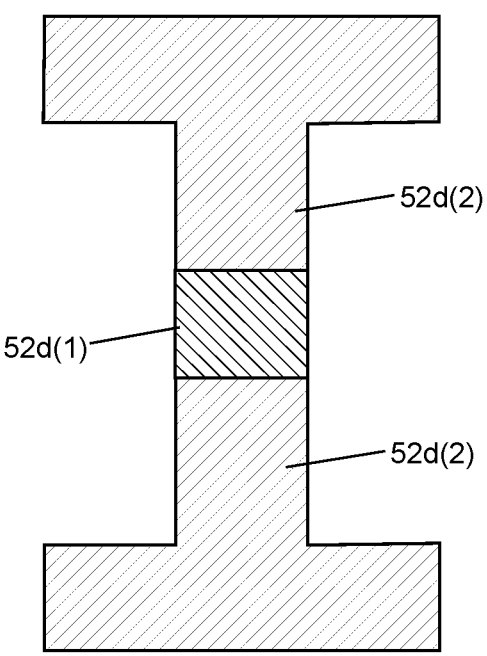
FIG. 5C  FIG. 5D

VALVES AND HUBS FOR TUBULAR DEVICES AND METHODS FOR MAKING AND USING THEM

This application is a continuation of co-pending U.S. application Ser. No. 16/436,873, filed Jun. 10, 2019, and issuing as U.S. Pat. No. 11,524,152, which claims benefit of U.S. provisional application Ser. No. 62/682,534, filed Jun. 8, 2018, the entire disclosures of which are expressly incorporated by reference herein.

FIELD OF THE INVENTION

The present invention relates generally to apparatus and methods for delivering instruments and/or agents during a medical procedure, and, more particularly, to valves and hubs for guide sheaths, catheters, and other tubular devices for accessing body lumens and/or for delivering instruments into body lumens of a patient, and to methods for making and using them.

BACKGROUND

There are many medical procedures where a guidewire, catheter, lead, and/or other medical device may be introduced into a patient's body cavity, recess, vessel, organ, and/or other body lumen. In many of these procedures, a delivery sheath, an access or guide catheter, or other tubular member including a valve on a proximal end thereof may be used to facilitate introducing medical devices into and through a lumen of the tubular device. It is generally desirable for the valve to provide a substantially fluid tight seal between the tubular device and the medical devices introduced therethrough, e.g., for the purpose of hemostasis, infusion of therapeutic or diagnostic agents, and the like.

With the advent of many large profile vascular access therapies (examples include percutaneous valve replacement systems, larger pulmonary vein isolation systems, and the like), the need for improved valve performance has been increasing. Current state of the art valves generally perform well for smaller profile medical devices. For example, the demands on a valve in a smaller access device, e.g., to seal around medical devices having sizes up to 8.5 French (2.8 mm), is much less as compared to an access device where the valve needs to seal over a range of devices up to ten French (10 Fr; 3.3 mm) or higher. While the list of problems with state of the art valves is long, the most significant problems are: 1) the inability to seal on a smaller device (such as a guidewire) after removal of a larger device (such as an ablation catheter), 2) the inability of the valve design to withstand prolonged use and wear (it may seal at the beginning at the beginning of a procedure but not over time as devices are removed and inserted), 3) high friction that is generally undesirable for the operator as well as contributing to valve wear and/or deterioration, and 4) complexity where multiple valve components are used serially and more complex operations are required.

By way of example, a cross-slit valve is a time-tested valve design used for many vascular access products that is simple and—in the case of smaller access devices—effective. For such valves, a pair of slits may be provided that extend entirely through the valve from opposite sides, crossing through each other to create a point or line that acts a subsequent sealing surface for devices that are passed through the valve. In general, the cross-slit valve performs well in positive and negative pressure conditions with nothing passed through the valve (the faces of each slit seal on themselves under the deflection that comes during positive or negative pressure).

However, such valves usually fail when a large device is placed through that causes the sidewalls of the material of the passage between the two slits to stretch beyond their limit. This leads to tearing or plastic deformation of the valve material or both. While the valve may continue to seal on the larger device (frequently not), it will not seal on smaller devices and, frequently, the tear prevents closure of the slits thus causing leaks in positive and negative pressure with nothing across the valve. Of very particular concern is air ingress, which may occur when a device is moved in or out or during aspiration from an access side port (a frequent occurrence for a host of reasons).

Moreover, most minimally invasive procedures require use of multiple devices of various sizes. For example, access is generally preserved with a guidewire during device exchanges and, over time, the valve may fail to maintain a seal after removal of secondary devices. In PVI (pulmonary vein isolation) cases, the primary ablation catheter is often removed and then mapping or touch-up devices are used (also frequently in conjunction with a guidewire).

For specific reference, state of the art elastomeric materials have a maximum elongation in the range of 1100% in softer materials (which are ideal for some purposes and problematic for others) and 500% or less in harder materials. In a cross-slit valve, the point or axis/line formed from the cross-slit must expand from a point surface diameter of theoretically zero to the largest sized device to go through (e.g., a dilator). While some hysteresis at the central point can prevent tearing, the elongation required to expand from this small effective diameter (e.g., around 0.005" (0.125 mm) to account for hysteresis prior to tearing) to that of say a 13 French (4.3 mm) dilator would require an elongation of over 3000%.

Valve performance in traditional valve designs has improved somewhat over the years as new or improved elastomers have come on to the market, both silicones as well as other natural and synthetic elastomers. However, those improvements are less and less, e.g., as very small increases in elongation, tear resistance, and the like may make little fundamental impact on valve performance. Some additional improvements have been made by incorporating multiple valves serially in a hub, but that adds complexity and new failure points.

Thus, sealing on small and large devices, particularly in the order where small devices must be inserted after use of a larger devices is an ongoing unmet clinical need of significant value.

SUMMARY

The present invention is directed generally to apparatus and methods for delivering instruments and/or agents during a medical procedure. More particularly, the present invention is related to valves and/or hubs for guide sheaths, catheters, and other tubular devices for accessing and/or delivering instruments into body lumens of a patient, and to methods for making and using them.

The ideal valve is a single part construction (for design robustness and manufacturability) that has one or more elements optimized for sealing in an empty condition and for sealing on secondary devices placed through/across the valve such that the valve material does not tear or otherwise deteriorate throughout its use and will continue to reliably seal on a range of secondary device diameters independent of the order of device usage The ideal valve minimizes friction and is ideally compatible with preferred lubricants. The ideal valve also makes insertion easy (e.g., is self-centering) both for ease of use and reduction in risk of damage to the valve.

The following disclosure describes exemplary valves and hubs for tubular devices that include one or more sealing elements for an "empty condition" (defined here as referring to when no device is introduced through or across the valve) and an additional but integral element/space for sealing on secondary devices, e.g., in a single construction. The empty condition sealing elements are generally accomplished with a cross-slit design where the cross-slit depths fall short of reaching each other, thus preserving a middle space without cross-slits for a secondary sealing element/space. A lumen or connecting hole may then be cut or otherwise formed between the cross-slits in a way that does not cut into the slit sidewalls near the faces (the two broad faces of the valve that are open to the outside of the device and this inside of the device) but fully connects the cross-slits to each other.

In an exemplary embodiment, unless directly formed in the valve prior to the cross-slits, the connecting hole may be formed by carefully bending/stretching/compressing or otherwise forming or moving the valve so that the hole cutting element can cut a hole only in the middle portion without cutting into the slit sidewalls at or near the faces. Thus, in the natural/non-bent condition, the connecting hole is otherwise concealed from view (unless transparent materials are used) from either face as the sidewalls of the cross-slits (both faces) fully close and block the view of the cavity/lumen connecting the two cross-slits just behind the closed sidewalls. Alternatively, the valve may be formed from multiple components, each including a set of one or more partial slits and a portion of a connecting hole, that may be applied together to provide a final valve.

In accordance with one embodiment, a valve is provided for a sheath, catheter, or other tubular device that includes a valve body comprising a first face, a second face opposite the first face and an axis extending between the first and second faces; a first slit extending from the first face towards the second face to a first intermediate location within the valve body; a second slit extending from the second face towards the first face to a second intermediate location within the valve body; and a bore extending along the axis between the first intermediate location and the second intermediate location.

In accordance with another embodiment, a valve is provided for a hub of a sheath, catheter, or other tubular device that includes a first valve portion formed from elastomeric material and comprising a first face, a first intermediate face opposite the first face and an axis extending between the first face and the first intermediate face, a first slit extending substantially parallel to the axis from the first face towards the first intermediate face to a first intermediate location within the first valve portion, and a first bore extending along the axis from the first intermediate location to the first intermediate face; and a second valve portion formed from elastomeric material and comprising a second face, a second intermediate face opposite the second face, a second slit extending substantially parallel to the axis from the second face towards the second intermediate face to a second intermediate location within the second valve portion, and a second bore extending along the axis from the second intermediate location to the second intermediate face, the first and second intermediate faces placed against one another such that first and second bores are aligned with one another to define a valve body.

In accordance with still another embodiment, a method is provided for making a valve for a sheath, catheter, or other tubular device that includes forming a resiliently flexible valve body comprising a first face, a second face opposite the first face and an axis extending between the first and second faces; forming a first slit extending substantially parallel to the axis from the first face towards the second face to a first intermediate location within the valve body; forming a second slit extending substantially parallel to the axis from the second face towards the first face to a second intermediate location within the valve body; and creating a bore extending along the axis from the first intermediate location to the second intermediate location.

In accordance with yet another embodiment, a method is provided for making a valve for a sheath, catheter, or other tubular device that includes forming a first valve portion comprising a first face, a first intermediate face opposite the first face and an axis extending between the first face and the first intermediate face, a first slit extending substantially parallel to the axis from the first face towards the first intermediate face to a first intermediate location within the first valve portion, and a first bore extending along the axis from the first intermediate location to the first intermediate face; forming a second valve portion comprising a second face, a second intermediate face opposite the second face, a second slit extending substantially parallel to the axis from the second face towards the second intermediate face to a second intermediate location within the second valve portion, and a second bore extending along the axis from the second intermediate location to the second intermediate face; and placing the first and second intermediate faces against one another such that first and second bores are aligned with one another to define a valve body.

Other aspects and features of the present invention will become apparent from consideration of the following description taken in conjunction with the accompanying drawings.

BRIEF DESCRIPTION OF THE DRAWINGS

The drawings illustrate exemplary embodiments of the invention, in which:

FIG. 1C is a cross-sectional view of yet another exemplary embodiment of a tubular device including a slittable hub on its proximal end and a valve secured to the hub.

FIG. 1C(1) is a detail showing an axis of a valve passage offset relative to a central axis of the tubular device of FIG. 1C.

FIGS. 5A-5D are cross-sectional side of views of alternative valves formed from multiple materials.

DETAILED DESCRIPTION OF THE EXEMPLARY EMBODIMENTS

Before the exemplary embodiments are described, it is to be understood that the invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and exemplary methods and materials are now described.

Figure 1A:
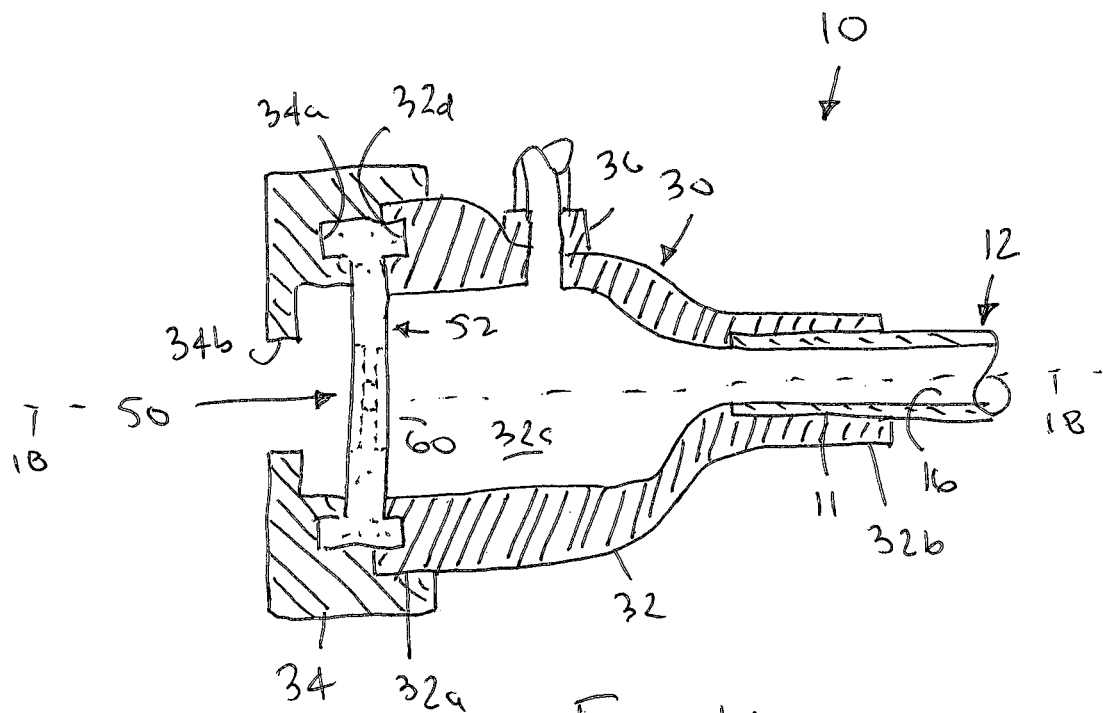
FIG. 1A is a cross-sectional side view of an exemplary embodiment of a tubular device including a hub on its proximal end and a valve secured within the hub.

Turning to the drawings, FIG. 1A shows an exemplary embodiment of an apparatus 10 for accessing a body lumen (not shown) and/or for delivering one or more fluids, agents, and/or instruments (also not shown) within a body lumen that may include a valve 50 according to any of the embodiments described herein. In exemplary embodiments, the apparatus 10 may be a guide catheter, a procedure catheter, an access sheath, or other tubular device sized for introduction into a body lumen, such as a vessel within a patient's vasculature, a passage within a patient's gastrointestinal tract, urogenital tract, reproductive tract, respiratory tract, lymphatic system, and the like.

Generally, the apparatus 10 includes an elongate tubular body 11 including a proximal end 12, a distal end sized for introduction into a body lumen (not shown), a lumen 16 extending between the proximal and distal ends along a central longitudinal axis 18, and a handle or hub 30 on the proximal end 12 including a valve 50 for allowing one or more devices to be introduced and/or fluids to be infused into the lumen 16. Optionally, the apparatus 10 may include one or more additional lumens (not shown), which may be disposed concentrically around, side-by-side with, or otherwise adjacent the lumen 16. The lumen 16 may be sized for receiving a guide wire, procedure catheter, cardiac lead, needle, or other instrument (not shown), and/or for delivering fluids or other flowable agents or materials therethrough, as described further elsewhere herein.

The tubular body 11 may be constructed from one or more layers, e.g., an inner liner surrounding the lumen 16, a reinforcing layer surrounding the inner liner, and an outer layer (not shown). Optionally, one or more coatings (also not shown) may be applied to the inner surface of the inner liner. In an exemplary embodiment, a hydrophilic coating, such as Polyvinylpyrrolidone, may be sprayed or otherwise applied onto the surface of the inner liner during fabrication to provide a lubricious inner surface for the lumen 16 of the tubular body 11. The layers of the tubular body 11 may be attached to one another, e.g., by laminating, adhering, adhesive bonding, ultrasonic welding, reflowing or other heating, and the like. Exemplary materials and methods for making the tubular body 11 are disclosed in co-pending applications Ser. No. 11/340,904, filed Jan. 26, 2006, Ser. No. 11/670, 958, filed Feb. 2, 2007, Ser. No. 12/254,818, filed Oct. 20, 2008, and Ser. No. 12/551,540, filed Aug. 31, 2009, the entire disclosures of which are expressly incorporated by reference herein.

The construction of the tubular body 11 may be substantially uniform or may vary between the proximal and distal ends, e.g., by varying the construction of the inner liner, reinforcing layer, and/or outer layer along the length of the tubular body 11. For example, the outer layer at or adjacent the proximal end 12 may be substantially rigid or semi-rigid, e.g., providing sufficient column strength to facilitate the apparatus 10 being pushed and/or otherwise manipulated from the proximal end 12. In addition, the reinforcing layer or the material of the outer layer may allow the apparatus 10 to be twisted from the proximal end 12, e.g., to rotate the distal end within a patient's body. Thus, the distal end of the apparatus 10 may be manipulated within a patient's body from the proximal end 12 without substantial risk of buckling and/or kinking. Optionally, the outer layer at or adjacent the distal end may be substantially flexible or semi-rigid, e.g., to allow the distal end to bend easily or otherwise be advanced through tortuous anatomy and/or provide a substantially atraumatic distal tip. Exemplary outer layers that may be included in the apparatus 10 and methods for making them are disclosed in U.S. Pat. Nos. 4,478,898, 4,863,442, 5,217,440, 5,254,107, 5,676,659, 5,811,043, 5,836,926, 6,004,310, 6,669,886, 6,837,890, and 6,945,970, the entire disclosures of which are expressly incorporated by reference herein.

In exemplary embodiments, the tubular body 11 may have an outer diameter between about half and twenty millimeters (0.5-20 mm) or between about one and five millimeters (1-5 mm), and a length between about five and one hundred fifty centimeters (5-150 cm). The inner liner may have a wall thickness between about 0.0001-0.01 inch (0.0025-0.25 mm) and the outer layer may have a wall thickness between about 0.0005-0.2 inch (0.0127-5.08 mm).

With continued reference to FIG. 1A, an exemplary embodiment of a hub 30 is shown that includes a first hub portion, e.g., hub body 32, and a second hub portion, e.g., cap 34, which may be coupled together, e.g., to secure a valve 50 within or to the hub 30. As shown, the hub body 32 may be an elongate tubular body including a first end 32a, a second end 32b, and a hub lumen 32c extending therebetween that communicates with the lumen 16 of the tubular body 11. The cap 34 may be connected to the first end 32a, e.g., using one or more of cooperating connectors, bonding with adhesive, sonic welding, fusing, interference fit and the like, to permanently (or alternatively, removably) capture the valve 50 within the hub 30.

Figure 1B:
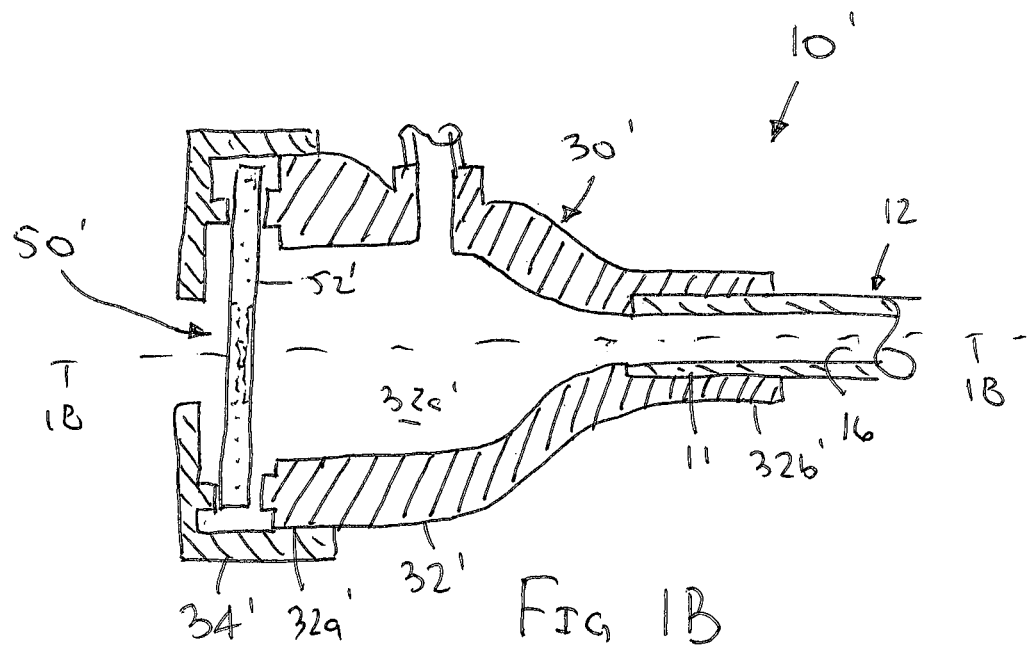
FIG. 1B is a cross-sectional side view another exemplary embodiment of a tubular device including a hub on its proximal end and a valve secured within the hub.

For example, as shown in FIG. 1A, the hub body 32 and cap 34 may include annular recesses 32d, 34a that receive a flange 70 on a perimeter of the valve 50, as described elsewhere herein. Alternatively, as shown in FIG. 1B, a valve 50' may be provided without a flange and a perimeter of the valve 50' may be captured by and/or otherwise secured between a hub body 32' and cap 34' of the hub 30.' In another alternative, shown in FIG. 1C, a valve 50" may be attached to a proximal end 30a" of a slittable hub 30," e.g., using one or more of cooperating connectors, bonding with adhesive, sonic welding, fusing, interference fit and the like, without a separate cap.

Returning to FIG. 1A, the second end 32b of the hub body 32 may include one or more connectors (not shown) for attaching the tubular body 11 to the hub 30. For example, the second end 32b may include one or more tabs, slots, threads, and the like (not shown) that may be engaged with complementary slots, tabs, threads, and the like (also not shown) on the proximal end 12 of the tubular body 11. In addition or alternatively, the second end 32b may be engaged with the proximal end 12 by an interference fit, may be attached by bonding with adhesive, fusing, sonic welding, heat bonding, reflowing, insert molding, and the like, if desired.

Optionally, the hub body 32 (or any of the other hubs herein) may also include one or more side ports, e.g., a first side port 36 communicating with the lumen 32c, e.g., to allow a source, e.g., a syringe, pump, air/vacuum line, and the like (not shown), to be coupled to the hub 30, e.g., to deliver fluid into the lumen 16 of the tubular body 11 and/or aspirate fluid from the lumen 16. Optionally, the cap 34 may include a transition, guide, or other features (not shown) at the opening 34b to guide and/or otherwise facilitate directing devices into the hub 30 and lumen 16 of the tubular body 11.

Figure 2A:
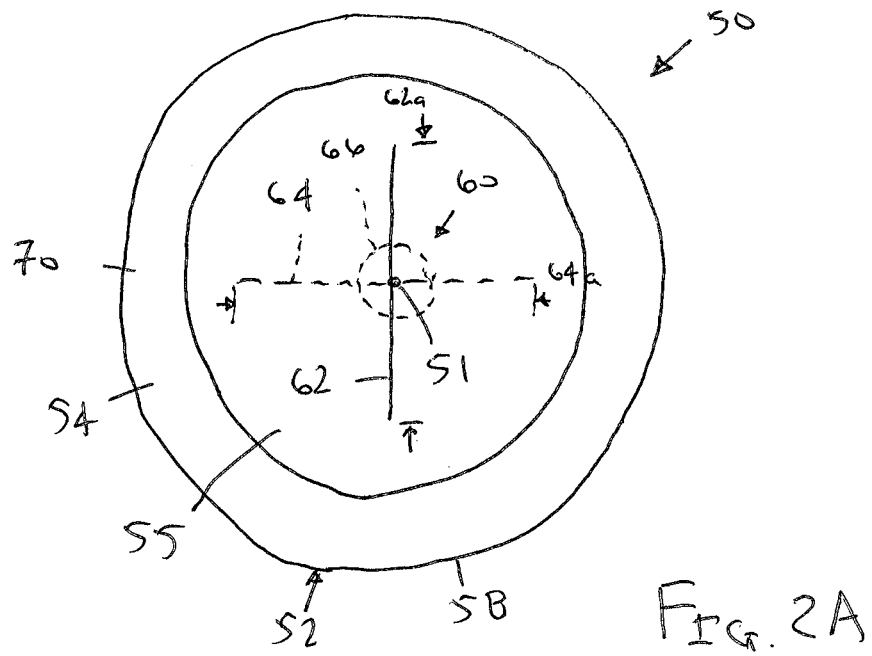
FIG. 2A is an end view of an exemplary embodiment of a valve that may be secured within the hub of FIG. 1A.
Figure 2B:
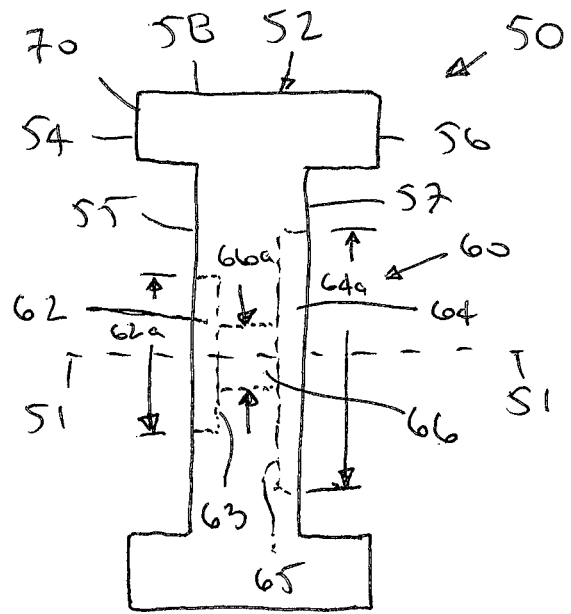
FIG. 2B is a cross-sectional side view of the valve of FIG. 2A.

Turning to FIGS. 2A-2B, an exemplary embodiment of a valve 50 is shown that may be received in the hub 30 shown in FIG. 1A. Generally, the valve 50 includes a valve body 52 including a proximal, inlet, or first end 54, a distal, outlet, or second end 56, an outer surface 58 extending between the first and second ends 54, 56, and a valve passage 60 extending between the first and second ends 54, 56, e.g., along an axis 51. As explained further below, the passage 60 is configured to provide a substantially fluid-tight seal when a medical device (not shown) is inserted into the valve 50 while also providing a fluid-tight seal when the valve passage 60 is empty (i.e., without a medical device inserted into the valve passage 60).

The valve body 52 includes a first face 55 adjacent the first end 54, and a second face 57 opposite the first face 55, i.e., adjacent the second end 56, with the passage 60 extending from the first face 55 to the second face 57. The faces 55, 57 may have a substantially circular shape, e.g., extending across a cross-section of the valve body 52, e.g., within the perimeter of the outer surface 58, as shown in FIG. 2A, or may have another desired shape, e.g., and oblong shape, and the like (not shown).

Optionally, the valve 50 may include an annular flange 70 extending around the perimeter of the valve body 52, e.g., surrounding the faces 55, 57. The flange 70 may have a thickness (i.e., dimension parallel to the axis 51) that is greater than the distance between the faces 55, 57, as shown in FIGS. 1A and 2B. Alternatively, as shown in FIG. 1B, the flange 70 may be omitted and the valve body 52' may have a uniform thickness within the outer surface 58, i.e., between the faces 55, 57. In a further alternative, a relatively thin intermediate annular region may be provided in the valve body (not shown), e.g., such that a relatively thicker central region includes the passage 60 and is surrounded by the intermediate region, and a relatively thicker outer perimeter is provided around the intermediate region, e.g., similar to the valve 150 shown in FIGS. 6A and 6B.

Figure 3A:
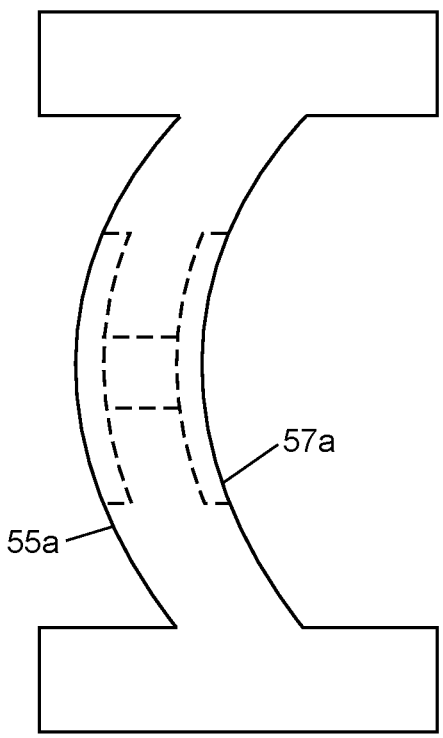
FIGS. 3A-3D are cross-sectional side views of alternative valves including non-planar faces.
Figure 3B:
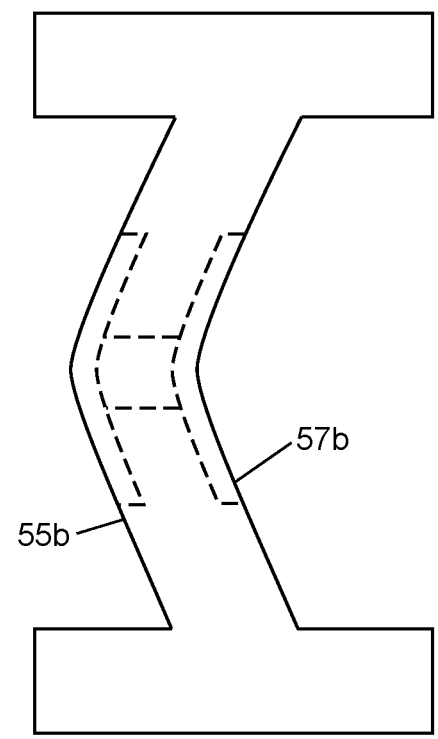
Figure 3C:
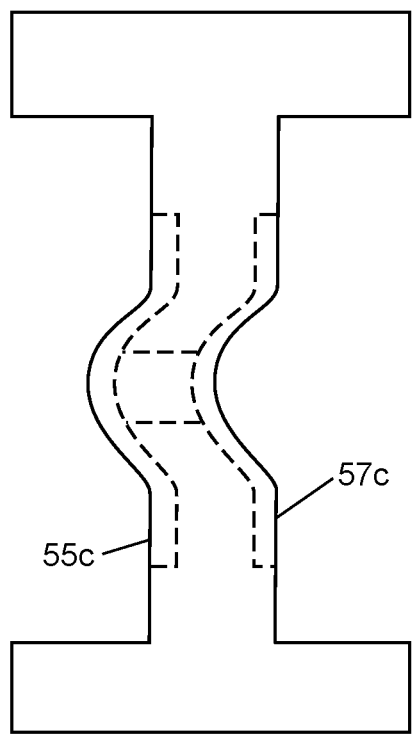

In the embodiment shown in FIGS. 2A and 2B, the faces 55, 57 are substantially planar, e.g., extending substantially perpendicular to the axis 51 of the valve 50. Alternatively, e.g., as shown in FIGS. 3A-3D, the faces 55, 57 may have other non-planar shapes. For example, FIG. 3A shows a valve where the first face 55a has a curved, e.g., convex, shape, and the second face 57a as a curved, e.g., concave, shape, e.g., such that a thickness of the valve between the faces 55a, 57a is substantially uniform. Alternatively, as shown in FIG. 3B, the faces may have corresponding frustoconical shapes, e.g., such that a thickness of the valve between the faces 55b, 57b is substantially uniform. In the embodiment shown in FIG. 3C, the faces 55c, 57c have planar outer annular regions and central regions having convex and concave shapes, e.g., such that a thickness of the valve between the faces 55c, 57c remains substantially uniform. Alternatively, in the embodiment shown in FIG. 3D, the faces 55d, 57d have planar outer annular regions and central regions having concave shapes, e.g., such that a thickness of the valve in the central regions is thinner than the outer regions.

Figure 3D:
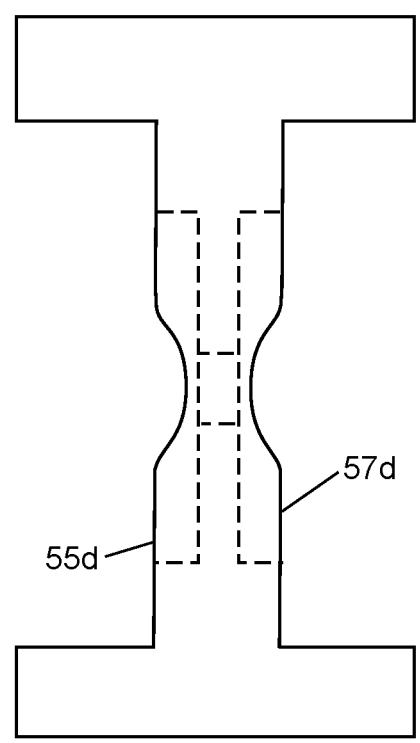

It will be appreciated that in these alternatives, optionally, a thickness of the valve body may be varied to provide desired mechanical properties and/or other advantages to the resulting valve. For example, providing a thicker outer region, as shown in FIG. 3D, may enhance support of the valve body, e.g., to resist tearing or plastic deformation of the valve adjacent the passage, while a thinner central region may facilitate opening the passage through the valve and/or reduce friction acting on devices introduced through the valve. In addition, the embodiments shown in FIGS. 3A-3C may provide enhanced sealing of the valve, e.g., when subjected to positive pressure from the first faces 55a-55c and/or negative pressure from the second faces 57a-57c.

Returning to FIGS. 2A and 2B, the passage 60 generally includes a first slit 62 extending substantially parallel to the axis 51 of the valve 50 from the first face 55 towards the second face 57 to a first intermediate location 63 within the valve body 52. Similarly, a second slit 64 extends from the second face 57 towards the first face 55 to a second intermediate location 66 within the valve body 52. A bore 66 extends along the axis 51 between the first intermediate location 63 and the second intermediate location 65. Thus, the central bore 66 may provide an interior or void region that may accommodate devices introduced through the passage 60, e.g., expanding while providing a contact surface against the devices to maintain a fluid-tight seal, while the slits 62, 64 may enhance sealing the passage 60 when devices are removed from the valve 50, e.g., resiliently closing such that opposite surfaces of the slits 62, 64 contact one another to seal the passage 60.

Figure 4A:
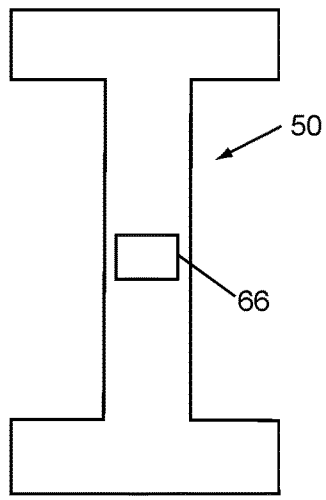
FIGS. 4A-4F are cross-sectional side of views of alternative valves including bores having various shapes.
Figure 4B:
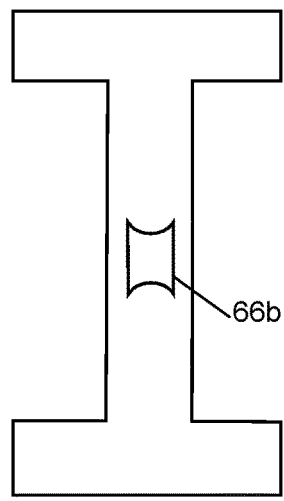
Figure 4C:
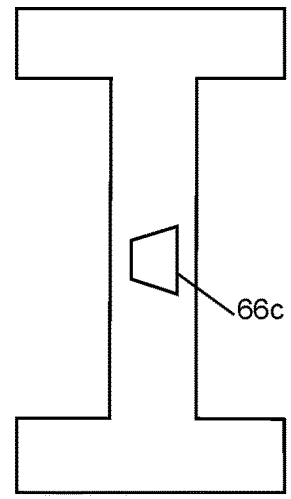
Figure 4D:
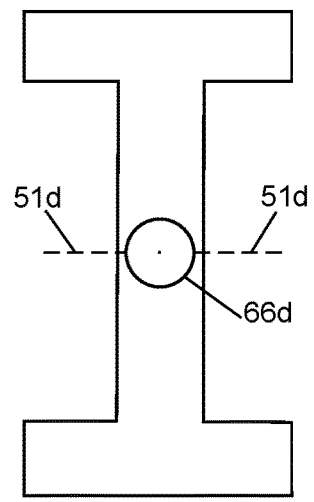
Figure 4E:
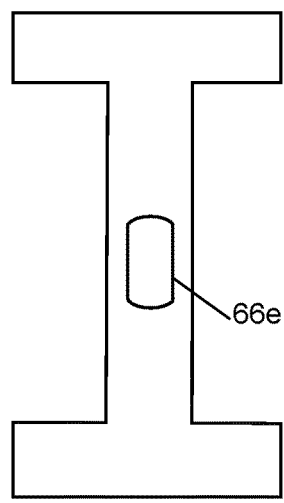
Figure 4F:
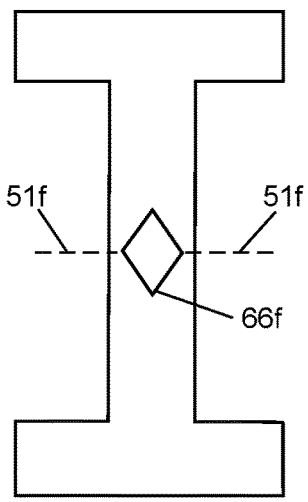

As shown in FIGS. 2B and 4A, the bore 66 may have a substantially uniform circular diameter extending between the intermediate locations 63, 65. Alternatively, the bore may have other shapes, e.g., a uniform non-circular cross-section extending between the intermediate locations (not shown). In further alternatives, as shown in FIGS. 4B-4F, the bore 66b-66f may have other non-uniform shapes. For example, FIG. 4B shows a bore 66b having an hourglass shape where the bore 66b tapers and expands between the intermediate locations, while FIG. 4E shows a bore 66e having a reverse hourglass shape, e.g., expanding and then tapering between the intermediate locations. FIG. 4C shows a bore 66c having a frustoconical or other expanding/reducing shape between the intermediate locations, e.g., having a circular or non-circular cross-section. FIG. 4D shows a bore 66d having a circular cross-section in a direction perpendicular to the axis 51*d* of the valve, although alternatively the bore 66*b* may have a spherical shape. FIG. 4F shows a bore 66*f* having a diamond cross-section in a direction perpendicular to the axis 51*f* of the valve.

As shown in FIG. 1A, the axis 51 of the valve 50 may be aligned with the longitudinal axis 18 of the hub 30 and tubular body 11, e.g., such that the passage 60 is centered on the hub 30. Alternatively, as shown in FIGS. 1C and 1C(1), the axis 51" of the valve 50" may be offset from the longitudinal axis 18, e.g., such that the slits 62", 64" and bore 66" are located is closer to the outer surface of the valve body 52" (and consequently, the hub 30") on one side than the opposite side. Consequently, a side wall region of the valve body 52" may be thinner on one side of the valve 50" than other side wall regions, which may facilitate slitting the valve 50" during use.

Returning to FIGS. 2A and 2B, the valve body 52 may be formed from an elastomeric material, such as silicone (e.g., having a durometer between about 30 A-50 A), chronoprene, isoprene, santoprene, and the like. Alternatively, other flexible synthetic or natural materials may be used for the valve body 52, e.g., thermoplastics, thermoset plastics, natural and synthetic rubbers, and the like. Within silicones, there are a range of LSR (liquid silicone rubber) material as well as HCR silicones (high consistency rubber) that may be used.

The valve body 52 may be formed from material having substantially uniform construction and/or mechanical properties. Alternatively, as shown in FIGS. 5A-5D, the valve body 52 may be formed from multiple materials, e.g., laminated or otherwise formed together, e.g., before creating the passage 60. For example, as shown in FIG. 5A, a valve body may be formed that includes a first material 52*a*(1) at the first end, a second material 52*a*(2) at an intermediate region between the first and second ends, and a third material 52*a*(3) at the second end. For example, the first and/or third materials 52*a*(1), 52*a*(3) may have greater elasticity and/or may be more resilient than the second material 52*a*(2), e.g., to ensure that the valve resiliently seals after removing a device from the valve. Alternatively, as shown in FIG. 5B, the valve body may include a central region 52*b*(1) encased within an outer material 52*b*(2) that provides material having desired elasticity and/or other properties where the passage is formed.

In a further alternative shown in FIG. 5C, the valve body may be formed from halves 52*c*(1) and 52*c*(2) having different properties from one another. In yet another alternative shown in FIG. 5D, the valve body may include a central region 52*d*(1) extending between the faces of the valve body formed from a first material, e.g., along the region defining the passage (not shown), and an outer material 52*d*(2) extending from the central region 52*d*(1) to an outer perimeter of the valve body, e.g., that provides material having desired elasticity and/or other properties where the passage is formed.

Optionally, e.g., in the case of silicone valves, the valve may be lubricated with silicone or other lubricant that may absorb into the valve providing some self-lubricating properties. Additionally, or alternatively, for example, a lubricant that won't absorb into the base material may be used (e.g., fluorinated silicone). In the case where both lubricants are used, the lubricant available on the surface may be useful for priming a dilator initially introduced through the valve. Such dilators are often the largest and "stickiest" device to go through a valve capable of applying the greatest stress to the valve. Thereafter, the absorbed lubricant may continue to lubricate other devices as the surface lubricant is used up.

In another embodiment, a silicone lubricant may be used with a silicone valve that may absorb the silicone causing the material to swell. In select geometries, the swelling is optimized to put the sidewalls of a cross-slit into compression with each other. Thus even a moderate bend which would usually begin opening the sidewalls form each other (opposite the side being bent together) does not initially open the sidewalls from each other. This increases performance consistency as any irregularity in the valve position or use that would otherwise have caused the sidewalls to open and thus leak (when nothing is across the web width) is now neutralized by the "negative" offset.

Returning to FIGS. 2A and 2B, in an exemplary embodiment, the valve body 52 may be formed from resiliently flexible material such that the bore 66 may be dilated or otherwise expanded when a medical device is inserted into the bore 66 and may resiliently return to its original size when the medical device is removed. Thus, the bore 66 may expand to accommodate a medical device having a larger cross-section than the bore 66 with the valve body 52 in the relaxed state. Similarly, the flexibility of the material may allow the sides of the slits 62, 64 to separate to accommodate introducing a device through the passage 60 and then the sides may resiliently close once the device is removed. Alternatively, the bore 66 may be sized appropriately to allow a medical device (not shown) to pass freely through the bore 66 without substantial frictional resistance and/or to provide a seal around the medical device to prevent substantial fluid leakage when the medical device is passed through the bore 66.

In the embodiment shown in FIGS. 2A and 2B, a single slit 62, 64 is provided extending inwardly from each of the opposite faces 55, 57 of the valve 50. Further, as shown in FIG. 2A, the slits 62, 64 may be offset from one another about the axis 51, e.g., offset about ninety degrees (90°). Alternatively, a pair of cross-slits may be provided instead for one or both slits 62, 64. Each such set of cross-slits may be substantially orthogonal to one another, e.g., offset about ninety degrees (90°) from one another and centered on the axis 51.

As shown in FIGS. 2A and 2B, the slits 62, 64 have corresponding widths 62*a*, 64*a* across the first and second faces 55, 57, respectively. The widths 62*a*, 64*a* may be symmetrical relative to the axis 51. In one embodiment, the widths may be substantially the same. Alternatively, one of the widths may be longer than the other. The widths of the slits 62, 64 may be sufficient to allow opposing regions of the valve body 52 on either side of the slit 64 to be directed away from one another to accommodate receiving a medical device through the passage 60 without substantial risk of the valve body 52 tearing uncontrollably. Thus, the valve body 52 may be resiliently flexible such that the opposing slit regions may expand when a medical device is inserted through the slits 62, 64, yet resiliently close when the medical device is removed to maintain a substantially fluid tight seal through the valve passage 60. In an exemplary embodiment, the widths 62*a*, 64*a* of the slits 62, 64 may be greater than half the perimeter of the largest device to be put through the passage 60 to reduce the chance of propagating a tear across the valve body 52.

With the valve body 52 in the relaxed state or empty condition (e.g., without a medical device inserted into the bore 62), the bore 62 may have a diameter or other maximum cross-section between about 0.25 and eight millimeters (0.25-8 mm), e.g., not more than about 0.030 inch (0.75 mm), but may be expandable to larger diameters, e.g., between about 0.35 and ten millimeters (0.35-10 mm). For example, silicone materials may be capable of elastically expanding about 1000% to accommodate a relatively large secondary device and still seal on a typical guidewire after the device is removed.

Returning to FIG. 2B, the first slit 62, second slit 64, and bore 66 may have corresponding lengths along the axis 51, i.e., to extend through the valve body 52 between the first and second faces 55, 57. In an exemplary embodiments, the lengths may be substantially the same, e.g., such that each extends about one third the distance between the first and second faces 55, 57. Alternatively, the lengths of the components of the passages 60 may be modified as desired to modify the mechanical properties of the valve 50.

In an exemplary embodiment, the outer/proximal slit of a valve (e.g., the slit 62 on the face 55 closest to the entrance to the valve hub 30, as shown in FIG. 1A) may have a longer length than the distal slit 57 since the proximal slit 55 only needs to seal at a maximum negative pressure, e.g., due to exposure to atmosphere (−14.7 psi), as opposed to the inner/distal slit 57, which generally provides a seal against positive pressure, which can be much larger. For example, if a syringe, power injector, or other device applies a pressure within the interior 32c of the hub 30, e.g., via the side port 36, the distal slit 57, the distal 57 may be exposed to pressures substantially greater than atmosphere, at least about 25 psi or more.

For example, for a valve of a given material and thickness, increasing the length (along the axis 51) of one or both of the slits 62, 64 may result in lower sealing pressures (positive and vacuum) as the increased length reduces the stiffness of the valve 50. This stiffness may keep the valve core from bending too far since the slit faces continue to seal against themselves, thus leading to failure at a lower pressure. Additionally, cross-slits that are too deep result in a remaining core that is relatively short and more prone to leaking on devices placed through the valve 50. Alternatively, deep cross-slits also help with centering the secondary device and lower friction acting on secondary devices.

The valve body 52 may be formed from a single piece of material or a composite body, e.g., molded, case, machined, laminated, and/or otherwise formed from desired material. In an exemplary method, a resiliently flexible valve body may be formed, e.g., from elastomeric material, that includes a first face, a second face opposite the first face and an axis extending between the first and second faces. A first slit may be cut or otherwise formed that extends substantially parallel to the axis from the first face towards the second face to a first intermediate location within the valve body. Similarly, a second slit may be cut or otherwise formed that extends substantially parallel to the axis from the second face towards the first face to a second intermediate location within the valve body. The first and/or second slits may be created by directing a cutting element into the first face or second face to a desired depth, e.g., without cutting beyond the first or second intermediate locations.

In addition, a bore may be created that extends along the axis from the first intermediate location to the second intermediate location. In one embodiment, the bore may be created by opening the first slit and directing a tool through the open first slit to create the bore, e.g., to mechanically cut, core, laser cut, or otherwise form the bore along the desired length of the valve body. Alternatively, the valve body may be formed, e.g., molded, cast, and the like, with an insert positioned at a location corresponding to the bore. Once the valve body is formed, one of the slits may be opened to allow the insert to be removed, thereby creating the bore. In exemplary embodiments, the insert may be a cylindrical or spherical element, e.g., a bee-bee or other component, formed from material that does not melt or otherwise deteriorate under the conditions for forming the valve body. Optionally, the insert may be coated with Teflon or other non-stick material, e.g., to facilitate removal of the insert after forming the valve body.

In one embodiment, the valve body 52 may be integrally formed as a single piece, e.g., by injection molding, casting, and the like. Alternatively, the valve body may be formed from multiple components that are fabricated separately and then attached together to provide a desired valve.

Figure 6A:
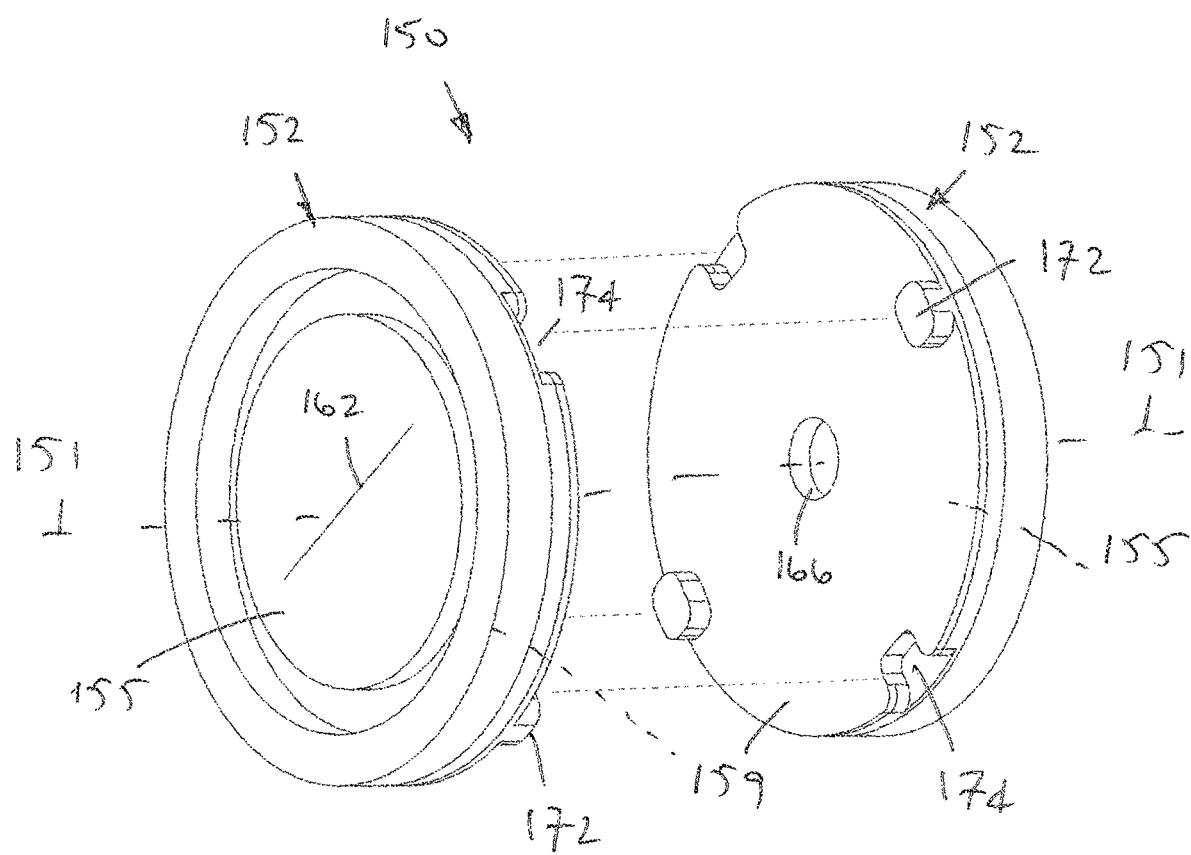
FIGS. 6A and 6B are perspective views of another embodiment of a valve formed from two valve portions.
Figure 6B:
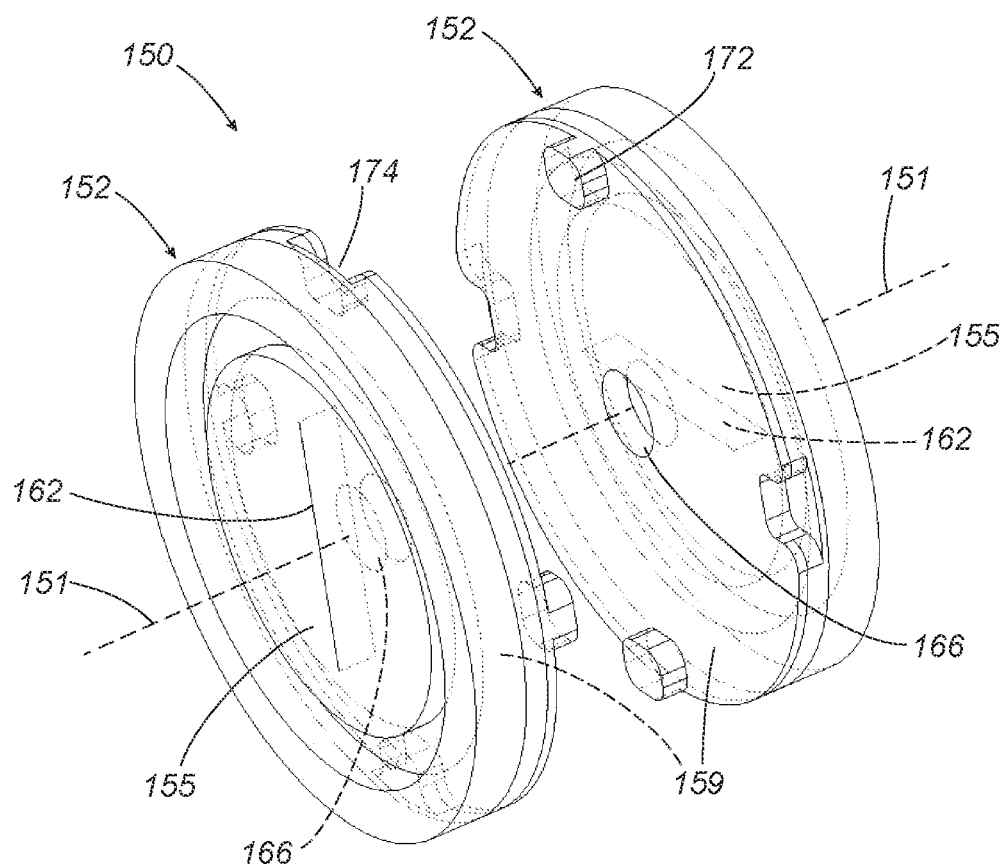
Figure 6C:
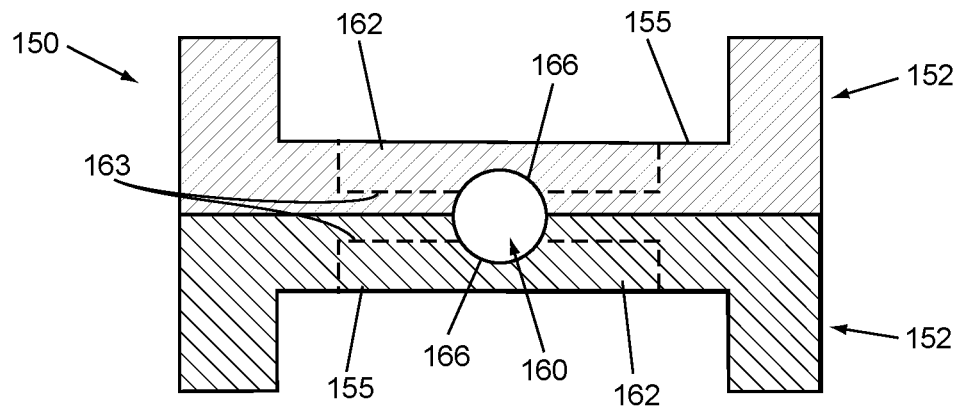
FIG. 6C is a cross-sectional view of a valve formed from the valve portions shown in FIGS. 6A and 6B.

For example, FIGS. 6A-6C show an exemplary valve 150 that includes first and second valve portions 152 that may be formed separately, e.g., by one or more of molding, casting, machining, laser cutting, and the like, whereupon the portions 152 may be positioned against and/or attached to one another to provide a passage 160 extending between opposite faces 155 of the final valve 150. In the embodiment shown, the valve portions 152 may be symmetrical and/or substantially identical to one another, e.g., such that intermediate surfaces 159 of the valve portions 152 may be placed against and substantially permanently (or removably) attached together, e.g., using one or more of cooperating connectors, bonding with adhesive, sonic welding, fusing, and the like.

As shown, each valve portion 152 includes a first or outer face 155, an intermediate face 159 opposite the outer, and a slit 162 extending substantially parallel to an axis 151 of the valve 150 from the first face 155 towards the intermediate face 159 to an intermediate location 163 within the valve portion 152. In addition, each valve portion 152 includes a bore 166 extending along the axis 151 from the intermediate location 163 to the intermediate face 159. Consequently, when the valve portions 152 are oriented with the intermediate faces 159 oriented towards and placed against one another, the bores 166 are aligned with one another to define an internal bore within the valve 150, e.g., as shown in FIG. 6C.

Optionally, the valve portions 152 may include one or more alignment or interlocking elements for aligning the intermediate faces together in a predetermined orientation. For example, as shown in FIGS. 6A and 6B, each valve portion 152 may include tabs 172 and recesses 174, e.g., spaced around a perimeter of the valve portion, such that the valve portions 152 may be rotated around the axis 151 until the tabs 172 are aligned with corresponding recesses 174 in the other valve portion 152. In the example shown in FIGS. 6A and 6B, each valve portion 152 includes two tabs 172 offset ninety degrees from two recesses 174 such that two identical valve portions 152 may be offset ninety degrees from one another and then attached together such that the slits 162 are also offset ninety degrees relative to the axis 151.

Figure 7A:
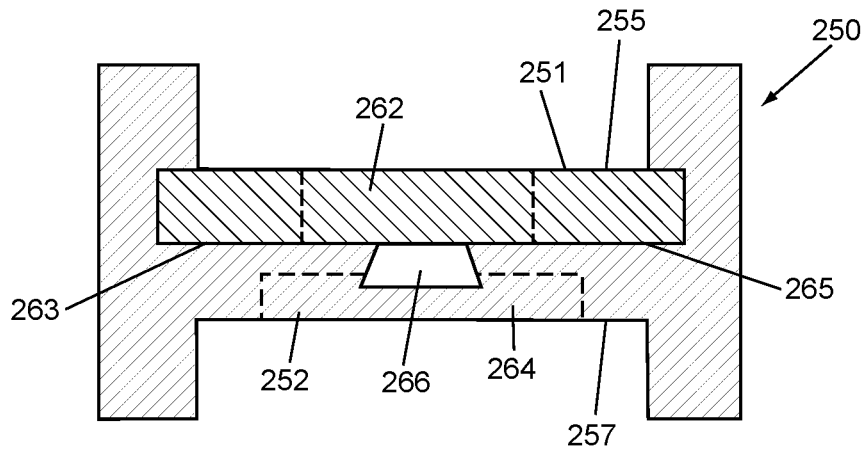
FIGS. 7A and 7B are cross-sectional views of alternative valves formed from multiple valve portions.

It will be appreciated that other alignment features and/or configurations may be provided. For example, as shown in FIG. 7A, a valve 250 may be provided that include first and second valve portions 251, 252 that are not identical. In the embodiment shown, the first valve portion 251 includes a first slit 262 that extends entirely through the first valve portion 251, e.g., from a first face 255 to a first intermediate face 263. The second valve portion 252 includes a second slit 264 that extends partially through the second valve portion 252 from a second face 257 to an intermediate location within the second valve portion 252, and a bore 266 that extends from the intermediate location to a second intermediate face 265. The first valve portion 251 may be received within and/or otherwise coupled to the second valve portion 252, as shown in FIG. 7A, such that the first slit 262 is aligned with the bore 266, e.g., to provide a passage through the valve 250 for receiving one or more devices, similar to other embodiments herein.

Figure 7B:
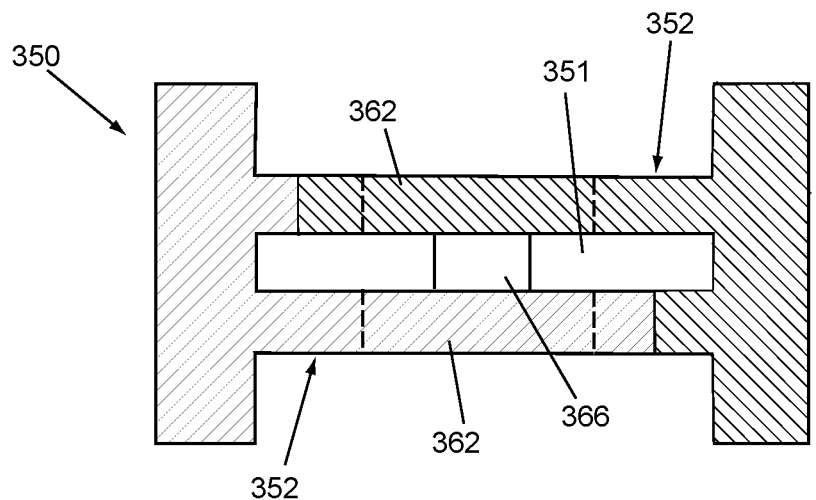

Turning to FIG. 7B, another embodiment of a valve 350 is shown that includes symmetrical outer valve portions 352 that include slits 362, and an intermediate valve portion 351 that includes a bore 366. The portions 351, 352 may be formed separately similar to any of the embodiments herein, and then assembled together to positon the intermediate valve portion 351 between the outer valve portions 352 such that the slits 362 are aligned with the bore 366 to provide a passage through the valve 350 for receiving one or more devices, similar to other embodiments herein. These alternatives may facilitate fabrication of a valve including an internal bore since the bore can be formed during molding or otherwise cut or formed in an exposed surface of the appropriate portion (portion 251 or 351), which may facilitate manufacturing.

The foregoing disclosure of the exemplary embodiments has been presented for purposes of illustration and description. It is not intended to be exhaustive or to limit the invention to the precise forms disclosed. Many variations and modifications of the embodiments described herein will be apparent to one of ordinary skill in the art in light of the above disclosure.

Further, in describing representative embodiments, the specification may have presented the method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A valve for a hub of a sheath, catheter, or other tubular device, comprising:
 a valve body comprising a first face, a second face opposite the first face and an axis extending between the first and second faces;
 a first slit having a first width perpendicular to the axis that is less than a width of the first face and a first length extending substantially parallel to the axis from the first face towards the second face to a first intermediate location within the valve body;
 a second slit having a second width perpendicular to the axis that is less than a width of the second face and a second length extending substantially parallel to the axis from the second face towards the first face to a second intermediate location within the valve body; and
 a bore extending along the axis between the first intermediate location and the second intermediate location such that the first slit and the second slit are spaced apart axially from one another on either side of the bore, the bore having a cross-section perpendicular to the axis that is smaller than the first width and the second width,
 wherein the valve body comprises:
 a first valve portion comprising the first face and first slit and defining a first intermediate face,
 a second valve portion comprising the second face and second slit and defining a second intermediate face,
 the first and second intermediate faces placed against one another to provide the valve body.

2. The valve of claim 1, wherein the first slit and the second slit intersect the axis and the bore surrounds between the first intermediate location and the second intermediate location.

3. The valve of claim 1, wherein the valve body comprises a perimeter surrounding the first and second faces.

4. The valve of claim 3, wherein the valve body has a first thickness along the axis between the first and second faces, and the perimeter has a second thickness along the axis greater than the first thickness.

5. The valve of claim 1, wherein the first slit comprises a first pair of crossed-slits extending from the first face to the first intermediate location.

6. The valve of claim 5, wherein the second slit comprises a second pair of crossed-slits extending from the second face to the second intermediate location.

7. The valve of claim 1, wherein the second width is shorter than the first width.

8. The valve of claim 1, wherein the second width is offset around the axis from the first width.

9. The valve of claim 1, wherein the first slit is oriented orthogonally relative to the axis from the second slit.

10. The valve of claim 1, wherein the axis is offset from a center of the first and second faces such that the bore is closer to one side of the valve body.

11. The valve of claim 1, wherein the valve body is resiliently flexible such that a cross-section of the bore may be increased and the first and slits may be opened to accommodate receiving an instrument through the valve body while maintaining a substantially fluid tight seal around the instrument.

12. The valve of claim 1, wherein the first and second faces are substantially flat.

13. The valve of claim 1, wherein the first face has a convex shape and the second face has a concave shape.

14. The valve of claim 1, wherein the bore has a circular cross-section between the first and second intermediate locations.

15. The valve of claim 1, wherein the bore has a non-circular cross-section between the first and second intermediate locations.

16. The valve of claim 1, wherein the valve body comprises elastomeric material.

17. The valve of claim 1, wherein the first valve portion includes a first bore portion extending from the first intermediate face towards the first face, and the second valve portion includes a second bore portion extending from the second intermediate face towards the second face, the first and second bore portions defining the bore when the first and second intermediate faces placed against one another.

18. A valve for a hub of a sheath, catheter, or other tubular device, comprising:
 a first valve portion formed from elastomeric material and comprising a first face, a first intermediate face opposite the first face and an axis extending between the first face and the first intermediate face, a first slit having a first width perpendicular to the axis and extending substantially parallel to the axis from the first face towards the first intermediate face to a first intermediate location within the first valve portion, and a first bore extending along the axis from the first intermediate location to the first intermediate face; and a second valve portion formed from elastomeric material and comprising a second face, a second intermediate face opposite the second face, a second slit having a second width perpendicular to the axis and extending substantially parallel to the axis from the second face towards the second intermediate face to a second intermediate location within the second valve portion, and a second bore extending along the axis from the second intermediate location to the second intermediate face, the first and second intermediate faces placed against one another such that the first and second bores are aligned with one another to define a valve body such that the first slit and the second slit are spaced apart axially from one another on either side of the first and second bores, wherein the first and second valve portions are formed from materials having different properties from one another, and the first and second bores having a cross-section perpendicular to the axis that is smaller than the first width and the second width.

19. The valve of claim 18, wherein the first and second valve portions comprise one or more connectors for coupling the first and second intermediate faces together.

20. The valve of claim 19, wherein the first and second intermediate faces are permanently attached together.

21. The valve of claim 19, wherein the first and second valve portions comprise perimeters surrounding the first and second faces, respectively.

22. The valve of claim 19, wherein each of the first and second valve portions comprises a central region, an annular region surrounding the central region, and an outer perimeter, the annular region having a thickness thinner than the central region and the perimeter.

23. The valve of claim 18, wherein the first and second valve portions comprise one or more alignment elements for aligning the first and second intermediate faces together in a predetermined orientation.

24. The valve of claim 23, wherein the one or more alignment elements orient the first and second slits such that the second width is offset around the axis from the first width.

* * * * *